United States Patent [19]

Hamby et al.

[11] Patent Number: 5,114,937
[45] Date of Patent: May 19, 1992

[54] RENIN INHIBITING NONPEPTIDES

[75] Inventors: James M. Hamby, Livonia; James S. Kaltenbronn; Joseph T. Repine, both of Ann Arbor, all of Mich.

[73] Assignee: Warner-Lambert Company, Morris Plains, N.J.

[21] Appl. No.: 442,952

[22] Filed: Nov. 28, 1989

[51] Int. Cl.$^5$ .................. A61K 31/395; C07D 265/30
[52] U.S. Cl. ........................... 514/238.2; 514/231.5; 514/238.8; 544/147; 544/159; 544/160; 544/162; 544/165; 544/168
[58] Field of Search ............. 544/147, 159, 160, 162, 544/165, 168; 514/231.5, 238.2, 238.8

[56] References Cited

U.S. PATENT DOCUMENTS 4,743,585 5/1988 Hudspeth et al. ................... 514/17
4,845,079 7/1989 Luly et al. ............................ 514/18

FOREIGN PATENT DOCUMENTS 0311012 4/1989 European Pat. Off. .

OTHER PUBLICATIONS

Stein and Marcotte, *MEDI*, Abst. 85, 194th ACS Meeting, New Orleans, Aug. 1987.
Kempf et al, *J. Med. Chem.*, 1990, 33:371-374.
Haber et al. J. Cardiovascular Pharm. vol. 10, Supp. 7, 1987 Balis et al. J. Med. Chem., 30, 1729-1737 (1987).
Burger. A. Medicinal Chem. 2nd Ed. 565-601 (1960)
Plattner et al. J. Medicinal Chem. (1988) 31, 2277-2288.

*Primary Examiner*—Johann Richter
*Attorney, Agent, or Firm*—Elizabeth M. Anderson

[57] ABSTRACT

The invention concerns novel renin-inhibitory compounds which are useful for treating renin-associated hypertension, congestive heart failure, hyperaldosteronism, glaucoma, and diseases caused by retroviruses including HTLV-I, -II, and -III. Processes for preparing the compounds, novel intermediates useful in the preparation thereof, compositions containing them, and methods of using them are included. Also included is a diagnostic method which uses the compounds to determine the presence of renin-associated hypertension, congestive heart failure, or hyperaldosteronism.

25 Claims, No Drawings

RENIN INHIBITING NONPEPTIDES

BACKGROUND OF THE INVENTION

Renin is a natural enzyme which is released into the blood from the kidney. It cleaves its natural substrate, angiotensinogen, releasing decapeptide, angiotensin I. This is in turn cleaved by converting enzyme in the lung, kidney, and other tissues to an octapeptide, angiotensin II. Angiotensin II raises blood pressure both directly by causing arteriolar constriction and indirectly by stimulating release of the sodium-retaining hormone aldosterone from the adrenal gland, causing a rise in extracellular fluid volume. Inhibitors of renins have been sought as agents for control of hypertension, congestive heart failure, hyperaldosteronism, and more recently, as agents for diseases caused by retroviruses including HTLV-I, -II, and III.

U.S. Pat. No. 4,743,585 covers renin-inhibiting peptides containing isosteres.

U.S. Pat. No. 4,845,079 covers renin-inhibiting peptidylaminodiols of formula

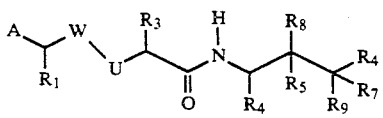

wherein A is a substituent; W is C=O or CHOH; U is $CH_2$ or $NR_2$, provided that when W is CHOH then U is $CH_2$; $R_1$ is loweralkyl, cycloalkylmethyl, benzyl, 4-methoxybenzyl, halobenzyl, (1-naphthyl)methyl, (2-napththyl)methyl, (4-imidazoyl)methyl, $\alpha,\alpha$-dimethylbenzyl, 1-benzyloxyethyl, phenethyl, phenoxy, thiophenoxy or anilino; $R_2$ is hydrogen or loweralkyl; $R_3$ is loweralkyl, [(alkoxy)alkoxy]alkyl, (thioalkoxy)alkyl, loweralkenyl, benzyl or heterocyclic ring substituted methyl; $R_4$ is loweralkyl, cycloalkylmethyl or benzyl; $R_5$ is vinyl, formyl, hydroxymethyl or hydrogen; $R_7$ is hydrogen or oweralkyl; $R_8$ and $R_9$ are independently selected from OH and $NH_2$; and $R_6$ is hydrogen, loweralkyl, vinyl or arylakyl; provided that when $R_5$ and $R_7$ are both hydrogen and $R_8$ and $R_9$ are OH, the carbon bearing $R_5$ is of the "R" configuration and the carbon bearing $R_6$ is of the "S" configuration.

The compounds covered by the references are useful as renin and acid protease inhibitors.

European Patent Application 311012 covers a method and a composition for treating or reducing and/or controlling intraocular pressure using a renin inhibiting compound.

SUMMARY OF THE INVENTION

The present invention concerns novel compounds which inhibit renin. It also concerns pharmaceutical compositions containing these novel compounds, methods of treating renin-associated hypertension, congestive heart failure, glaucoma, and hyperaldosteronism, as well as the use of the peptides as diagnostic tools, and the methods for preparing the compounds.

Since HIV protease, like renin, as an aspartyl protease, these compounds can also be used to treat diseases caused by retroviruses including HTLV-I, -II, and -III.

The compounds of the invention contain no amide bonds that connect natural amino acids. Consequently, these compounds show enhanced stability to enzymatic hydrolysis. This feature, in turn, leads to longer acting, orally active compounds.

A designation for the compounds of this invention is illustrated below. For example,

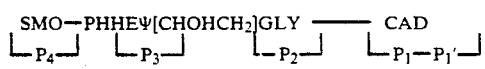
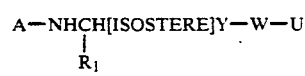

The compounds of this invention have an isostere connecting the $P_3$ and $P_2$ positions.

The present invention relates to novel compounds of formula $$A-NHCH[ISOSTERE]Y-W-U \qquad I$$
$$\underset{R_1}{|}$$

or a pharmaceutically acceptable acid addition salt thereof wherein A, Y, W, U, R, and isostere are as defined hereinbelow.

The invention also includes pharmaceutical compositions comprising an effective amount of the above compound of formula I in admixture with a pharmaceutically acceptable carrier or excipient and a method for treating renin-associated hypertension in a patient suffering therefrom comprising administering to said patient the above pharmaceutical composition in unit dosage form.

Further, the invention includes a pharmaceutical composition comprising an effective amount of a compound of formula I above in admixture with a pharmaceutically acceptable carrier or excipient, and a method for treating hyperaldosteronism in a patient suffering therefrom comprising administering to said patient the above pharmaceutical composition in unit dosage form.

Further, the invention includes a pharmaceutical composition comprising an effective amount of a compound of formula I in admixture with a pharmaceutically acceptable carrier or excipient, and a method for treating congestive heart failure in a patient suffering therefrom comprising administering to said patient the above pharmaceutical composition in unit dosage form.

Further, the invention includes a pharmaceutical composition comprising an effective amount of a compound of formula I in admixture with a pharmaceutically acceptable carrier or excipient, and a method for treating diseases caused by retroviruses including HTLV-I, -II, and -III.

Further, the instant invention includes a pharmaceutical composition comprising an effective amount of a compound of formula I in admixture with a pharmaceutically acceptable carrier or excipient and a method for lowering intraocular pressure, an anti-glaucoma agent, using the composition.

The present invention also includes the use of a compound of formula I above as a diagnostic tool for the identification of cases of hypertension due to renin excess.

The invention further includes methods for preparing compounds of formula I above and novel intermediates used in their preparation.

DETAILED DESCRIPTION

The following table provides a dictionary of the terms used in the description of the instant invention.

TABLE I

| Abbreviated Designation | |
|---|---|
| | Amino Acid |
| GLY | Glycine |
| PHE | L-Phenylalanine |
| CAD | 2(S)-Amino-3(R),4(S)-dihydroxy-1-cyclohexyl-6-methylheptane |
| CAH | 1(S)-Amino-2(R),3(S)-dihydroxy-1-cyclohexyl-5-methylhexane |
| ASTA | 3(R,S),4(S)-Diamino-6-methylheptanoic acid |
| ACYS | 3(R,S),4(S)-Diamino-5-cyclohexanepentanoic acid |
| DFSTA | 4(S)-Amino-3(S)-hydroxy-2,2-difluoro-6-methylheptanoic acid |
| DFKSTA | 4(S)-Amino-3-oxo-2,2-difluoro-6-methylheptanoic acid |
| DFCYS | 4(S)-Amino-3(S)-hydroxy-2,2-difluoro-5-cyclohexanepentanoic acid |
| DFKCYS | 4(S)-Amino-3-oxo-2,2-difluoro-5-cyclohexanepentanoic acid |
| | Acyl Group |
| Z | Benzyloxycarbonyl |
| BOC | Tert-butyloxycarbonyl |
| IVA | Isovaleryl |
| NVA | n-Valeryl |
| SMO | Morpholinosulfamyl |
| SME | Dimethylaminosulfamyl |
| | Amides With |
| AEM | 4-(2-Aminoethyl)morpholine |
| MBA | 2(S)-Methylbutylamine |
| —NHCH$_2$— (pyridyl) | 2-Aminomethylpyridine |
| —NHCH$_2$Ph | Benzylamine |
| —NHC$_4$H$_9$ | n-Butylamine |
| —NHCH$_3$ | Methylamine |
| —NHCH$_2$—(phenyl)—CH$_2$NH$_2$ | m-Xylene-di-amine |
| | Solvents and Reagents |
| HOBT | Hydroxybenzotriazole hydrate |
| DMF | N,N-Dimethylformamide |
| Et$_3$N | Triethylamine |
| DCC | N,N'-Dicyclohexylcarbodiimide |
| THF | Tetrahydrofuran |
| MeOH | Methanol |
| Et$_2$O | Diethyl ether |
| CDI | Carbonyldiimidazole |
| EtOH | Ethanol |
| TBDMS | Tert-butyldimethylsilane |
| TFA | Trifluoroacetic acid |
| HOAc | Acetic acid |
| EtOAc | Ethyl acetate |

Compounds of the instant invention are represented by formula

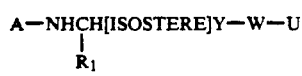

or a pharmaceutically acceptable acid addition salt thereof wherein:

A is hydrogen, BOC, Z, IVA, NVA, or

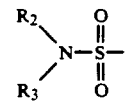

wherein R$_2$ and R$_3$ are each independently hydrogen, a straight or branched lower alkyl, or R$_2$ and R$_3$ when taken together with the nitrogen to which they are attached form a saturated 5- or 6-membered ring which may optionally contain an additional heteroatom: O, S, or NR$_3$, R$_1$ is CH$_2$Ph,

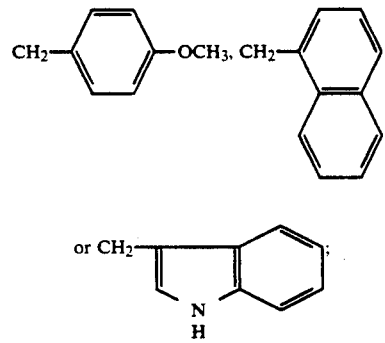

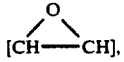

[isosterel] is [CHOHCH$_2$], [COCH$_2$], [CHOHCHOH], [CH=CH],

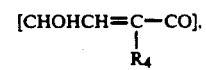

[CH$_2$NH], [CH$_2$NOH], [CH$_2$S], [CH(NH$_2$)CH$_2$], [CH$_2$SO], CH$_2$SO$_2$], [CH$_2$CH$_2$],

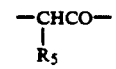

, [CHOHCHOHCHOHCO] or [CH$_2$O] wherein R$_\alpha$ is H, lower alkyl, lower alkenyl, lower alkynyl, CO$_2$R$_3$, arylmethyl, or heterocyclicmethyl;

Y is absent, or

—CHCO—
    |
    R$_5$ wherein

R$_5$ is hydrogen, OR$_6$, S(O)$_n$R$_6$, NR$_7$R$_8$ or NHCOR$_9$ wherein R$_6$ is lower alkyl, lower alkenyl, lower alkynyl, aryl, or heteroaryl, n is an integer of from 0 to 2, R$_7$ and R$_8$ are each independently hydrogen, lower alkyl, lower alkenyl, lower alkynyl, aryl or heteroaryl or when taken together with the nitrogen to which they are attached form a saturated 5- or 6-membered ring which may optionally contain an additional heteroatom, O, S, or NR$_3$, R$_9$ is hydrogen, lower alkyl or aryl with the proviso that when [ISOSTERE] is

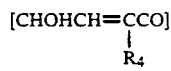

or [CHOHCHOHCHOHCO], Y is absent;

W is CAD, CAH, DFCYS, DFKCYS, DFSTA, DFKSTA, ASTA, ACYS or

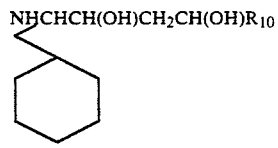

wherein
R₁₀ is lower alkyl or alkenyl; and
U is absent, AEM, MBA,

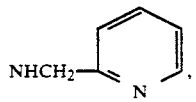

NHCH₂Ph, NHC₄H₉, NHCH₃ or

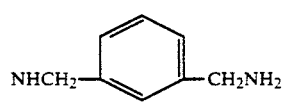

with the proviso that when W is CAD, CAH or NHCHCH(OH)CH₂CH(OH)R₁₀, U is absent.

Other compounds of the instant invention are those of Formula I wherein

A is hydrogen, BOC, Z, IVA, NVA, or

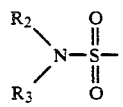

wherein R₂ and R₃ are each independently H, a straight or branched lower alkyl, or R₂ and R₃ when taken together with the nitrogen to which they are attached form a saturated 5- or 6-membered ring which may optionally contain an additional heteroatom: O, S, or NR₃, R₁ is CH₂Ph,

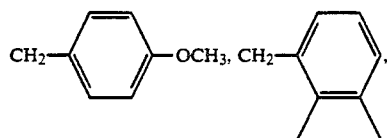

or 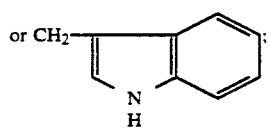

[isostere] is [CHOHCH₂], [COCH₂], [CHOHCHOH], [CH(NH₂)CH₂], CH=CH],

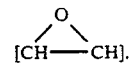

[CH₂NH], [CH₂NOH], [CH₂S], [CH₂SO], CH₂SO₂], [CH₂CH₂], or [CH₂O];

Y is

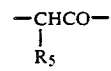

wherein R₅ is lower alkyl, lower alkenyl, lower alkynyl, arylmethyl or heterocyclicmethyl;

W is CAD, CAH, DFCYS, DFKCYS, DFSTA, DFKSTA, ASTA, ACYS or

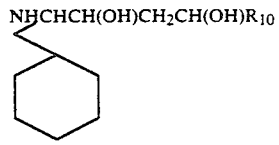

wherein R₁₀ is lower alkyl or alkenyl; and
U is absent, AEM, MBA,

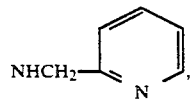

NHCH₂Ph, NHC₄H₉, NHCH₃ or

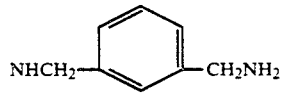

with the proviso that when W is CAD, CAH or NHCHCH(OH)CH₂CH(OH)R₁₀, U is absent.

Preferred compounds of the instant invention are those of formula I wherein

A is BOC, Z, SMO, SME,

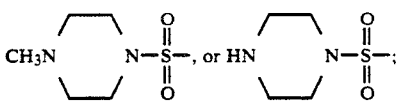

R₁ is CH₂Ph,

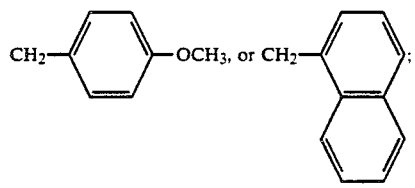

[isostere] is [CHOHCH₂], [COCH₂], [CH₂NH], CHOHCH=CHCO], [CHOHCH=C(CH₃)CO], CHOHCH=C(C₄H₉)CO], [CHOHCH=C(CH₂Ph)CO], or

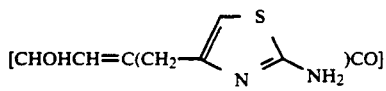

with the proviso that Y is absent when [isostere] is [CHOHCH=CHCO], [CHOHCH=C(C₄H₉)CO], [CHOHCH=C(CH₃)CO], CHOHCH=C(CH₂Ph-)CO], or

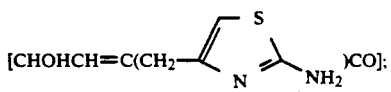

Y is

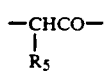

wherein $R_5$ is hydrogen, $OCH_3$, $OC_3H_7$, $OCH_2CH=CH_2$, $OCH_2C\equiv CH$, $SCH_3$, $SC_3H_7$, $SCH_2CH=CH_2$, $SCH_2C\equiv CH$, $NH_2$, $NHCH_3$, $N(CH_3)_2$,

or $NHCOCH_3$;

W is CAD, CAH, DFKCYS, DFKSTA,

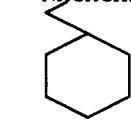

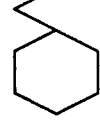

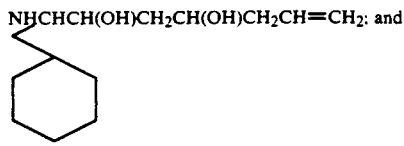

U is absent, AEM, $NHC_4H_9$,

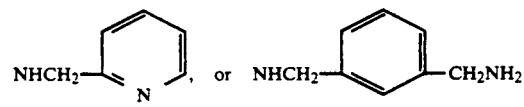

with the proviso that U is absent when W is CAD, CAH, or

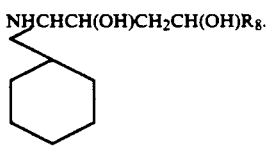

Other preferred compounds of the instant invention are those of formula I wherein Y is

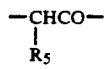

wherein $R_5$ is $CH_3$, $C_4H_9$, $CH_2CH=CH_2$, $CH_2C\equiv CH$, $CH_2Ph$,

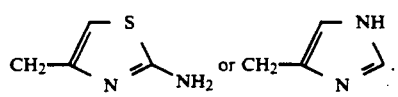

Most preferred compounds of the instant invention include but are not limited to:

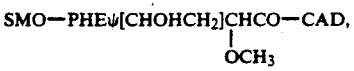

SMO—PHEψ[CHOHCH₂]CHCO—CAD,
        |
        SCH₂C≡CH

SMO—PHEψ[CHOHCH₂]CHCO—CAD,
        |
        NHCH₃,

SMO—PHEψ[CHOHCH₂]CHCO—CAD,
        |
        N(CH₃)₂

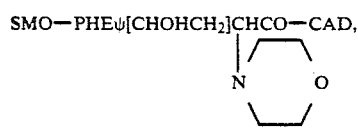

SMO—PHEψ[CHOHCH₂]CHCO—CAD,
        |
        NHC—CH₃
         ‖
         O

SMO—PHEψ[CHOHCH₂]CHCO—CAD,
        |
        NHPh

SMO—PHEψ[CHOHCH₂]CHCO—CAD,
        |
        SPh

SMO—PHEψ[CHOHCH₂]CHCO—CAD,
        |
        OPh

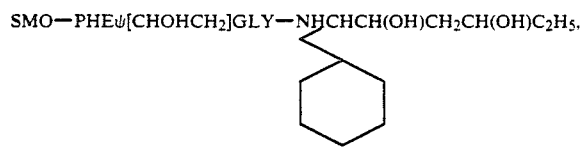

SMO—PHEψ[CHOHCH₂]GLY—NHCHCH(OH)CH₂CH(OH)C₂H₅,

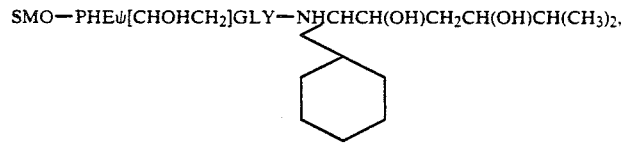

SMO—PHEψ[CHOHCH₂]GLY—NHCHCH(OH)CH₂CH(OH)CH(CH₃)₂,

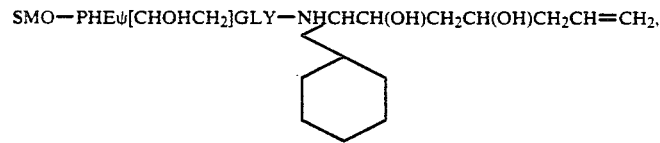

SMO—PHEψ[CHOHCH₂]GLY—NHCHCH(OH)CH₂CH(OH)CH₂CH=CH₂,

SMO—PHEψ[CHOHCH₂]GLY—CAH,

SMO—PHEψ[CHOHCH₂]GLY—DFKCYS—AEM,

SMO—PHEψ[CHOHCH₂]GLY—DFKSTA—AEM,

SMO—PHEψ[CHOHCH₂]GLY—ACYS—AEM,

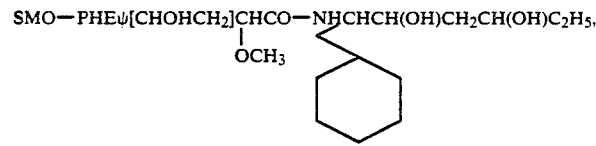

SMO—PHEψ[CHOHCH₂]CHCO—NHCHCH(OH)CH₂CH(OH)C₂H₅,
        |
        OCH₃

-continued
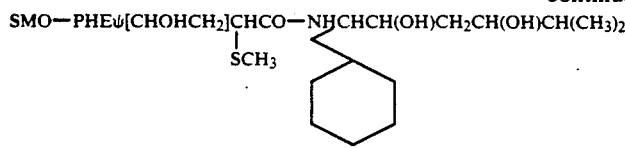
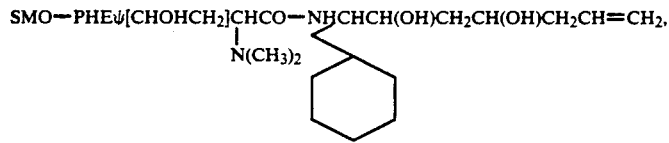
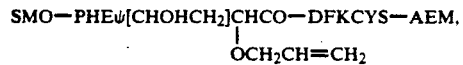
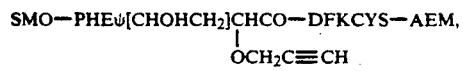
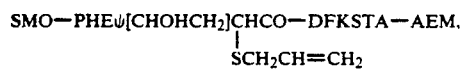
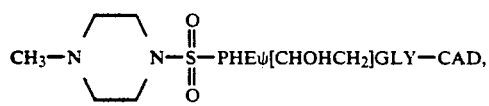
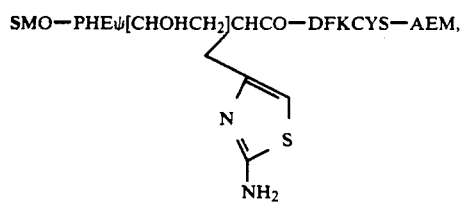
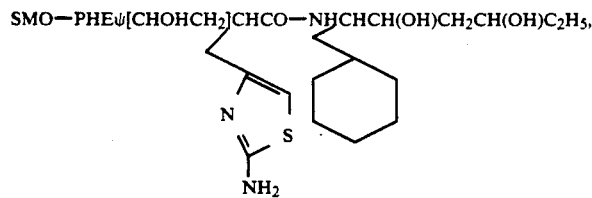
SMO—PHEψ[CH₂O]GLY—CAD,
SMO—PHEψ[CH₂NOH]GLY—CAD,
SMO—PHEψ[CH₂S]GLY—CAD,
SMO—PHEψ[CH₂SO]GLY—CAD,
SMO—PHEψ[CH₂SO₂]GLY—CAD,
SMO—PHEψ[CHOHCHOH]GLY—CAD,
SMO—PHEψ[CH₂CH₂]GLY—CAD,
SMO—PHEψ[CHOHCHOHCHOHCO]CAD,
SMO—PHEψ[CH=CH]GLY—CAD,
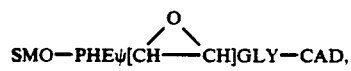

SMO—PHEψ[CHOHCH₂]CHCO—CAD,
                |
                NH₂

SMO—PHEψ[CHOHCH=C(CH₃)CO]CAD,

SMO—PHEψ[CHOHCH=C(C₄H₉)CO]CAD,

SMO—PHEψ[CHOHCH=C(CH₂Ph)CO]CAD,

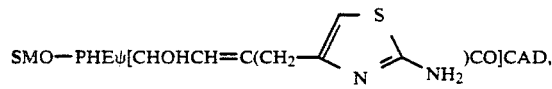

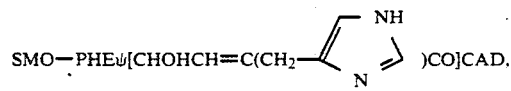

SMO—TYR(OMe)ψ[CHOHCH₂]CHCO—CAD,
                        |
                        OC₃H₇

SMO—TYR(OMe)ψ[CHOHCH₂]CHCO—CAD,
                        |
                        SCH₂C≡CH

SMO—TYR(OMe)ψ[CHOHCH₂]CHCO—CAD, and
                        |
                        NHCH₃

SMO—TYR(OMe)ψ[CHOHCH₂]CHCO—CAD.
                        |
                        OPh

Still other valuable compounds falling within the scope of the invention are:

SMO—PHEψ[CHOHCH₂]CHCO—CAD,
                |
                CH₃

SMO—PHEψ[CHOHCH₂]CHCO—CAD,
                |
                C₄H₉

SMO—PHEψ[CHOHCH₂]CHCO—CAD,
                |
                CH₂Ph

SMO—PHEψ[CHOHCH₂]CHCO—CAD,
                |
                CH₂CH=CH₂

SMO—PHEψ[CHOHCH₂]CHCO—CAD, and
                |
                CH₂C≡CH

-continued

SMO—PHEψ[CHOHCH₂]CHCO—CAD.

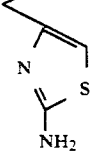

SMO—TYR(OMe)ψ[CHOHCH₂]CHCO—CAD,

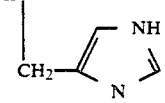

SMO—TYR(OMe)ψ[CHOHCH₂]CHCO—CAD,
                        |
                        C₄H₉

SMO—TYR(OMe)ψ[CHOHCH₂]CHCO—CAD, and
                        |
                        CH₂CH=CH₂

SMO—TYR(OMe)ψ[CHOHCH₂]CHCO—CAD,

The most preferred compounds of the instant invention are:

SMO—PHEψ[CHOHCH=CHCO]CAD,

BOC—PHEψ[CH=CH]GLY—CAD,

-continued

BOC—PHEψ[CH—O—CH]GLY—CAD,

SMO—PHEψ[COCH₂]GLY—CAD,

SMO—PHEψ[CHOHCH₂]GLY—CAD (Isomer A),

SMO—PHEψ[CHOHCH₂]GLY—CAD (Isomer B),

Z—PHEψ[COCH₂]GLY—CAD,

Z—PHEψ[CHOHCH₂]GLY—CAD (mixture of diastereomers),

Z—PHEψ[CHOHCH₂]GLY—CAD (slow eluting diastereomer).

PHEψ[CHOHCH₂]GLY—CAD,

BOC—PHEψ[CHOHCH₂]GLY—CAD (Mixture of diastereomers),

BOC—PHEψ[CHOHCH₂]GLY—CAD (slow eluting diastereomer),

SMO—PHEψ[CH₂NH]GLY—CAD,

BOC—PHEψ[CHOHCH₂]CHCO—CAD (Isomer A),
                              |
                             NH₂

BOC—PHEψ[CHOHCH₂]CHCO—CAD (Isomer B), and
                              |
                             NH₂

SMO—PHEψ[CH(NH₂)CH₂]GLY—CAD.HCl.

Novel intermediates of the instant invention include:

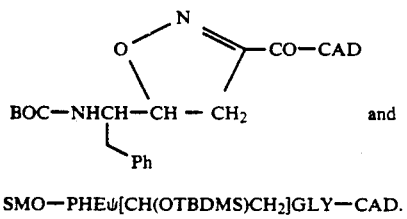

SMO—PHEψ[CH(OTBDMS)CH₂]GLY—CAD.

The compounds include solvates and hydrates and pharmaceutically acceptable acid addition salts of the basic compounds of formula I above.

The term pharmaceutically acceptable acid addition salt is intended to mean a relatively nontoxic acid addition salt either from inorganic or organic acids such as, for example, hydrochloric, hydrobromic, hydroiodic, sulfuric, phosphoric, acetic, citric, oxalic, malonic, salicylic, malic, benzoic, gluconic, fumaric, succinic, ascorbic, maleic, tartaric, methanesulfonic, and the like. The salts are prepared by contacting the free base form with a sufficient amount of the desired acid to produce a salt in the conventional manner. The free base forms may be regenerated by treating the salt form with a base.

The modified peptides of the present invention possess one or more chiral centers and each center may exist in the R(D) or S(L) configuration. The present invention includes all enantiomeric and epimeric forms as well as the appropriate mixtures thereof. Unless otherwise specified the L form is the preferred embodiment.

The term lower alkyl refers to straight or branched chain alkyl radicals containing from one to six carbon atoms including but not limited to methyl, ethyl, n-propyl, isopropyl, n-butyl, iso-butyl, sec-butyl, 2-methylhexyl, n-pentyl, 1-methylbutyl, 2,2-dimethylbutyl, 2-methylpentyl, 2,2-dimethylpropyl, n-hexyl, and the like.

The preferred lower alkyl groups are methyl, ethyl, n-butyl, and isobutyl.

The term arylmethyl refers to a radical of the formula -CH₂Ar where Ar can be phenyl, a phenyl substituted with OH, OCH₃, or halogen, or 1- or 2-naphthyl. The preferred groups are those where aryl is phenyl or p-methoxyphenyl.

The term saturated ring containing from two to five carbon atoms, which ring can optionally contain an additional O, S, or NR₃ is meant to include, for example,

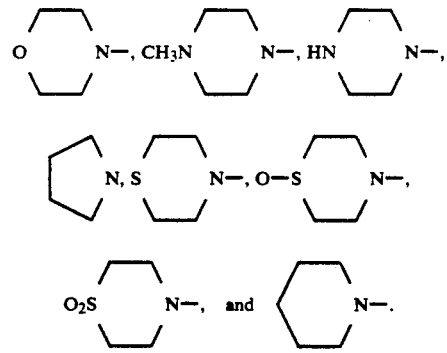

The preferred groups are

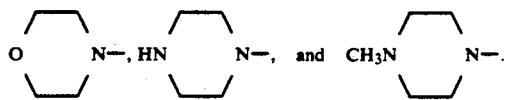

The term lower alkenyl refers to straight or branched chain alkenyl radicals containing two to six carbon atoms. The preferred groups are allyl and methylallyl.

The term lower alkynyl refers to straight or branched chain alkynyl radicals containing two to six carbon atoms. The preferred groups are —CH₂C≡CH and —CH₂C≡C—CH₃.

The term heterocyclicmethyl refers to a radical of the formula —CH₂-heterocycle, where the heterocycle can be a saturated or unsaturated five or six membered ring containing one or more heteroatoms selected from N, S, and O, and may be optionally substituted with OH, NH₂, or NR₂R₃ where R₂ and R₃ have the designation previously described. The preferred radicals embodied in this description are

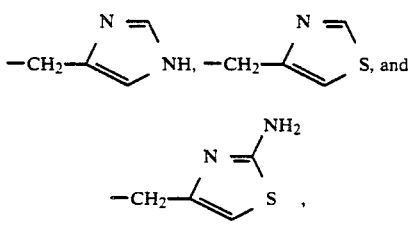

and the regioisomers thereof.

The term isostere means that the atoms enclosed in brackets replace the normal amide bond of the peptitde. The symbol Ψ means that the following atoms in brackets constitute an isostere.

Heteroaryl means a substituted or unsubstituted aromatic ring containing at least one heteroatom selected from O, S, and N and from three to five carbon atoms. The preferred heteroaryls are imidazoles, thiazoles, and amino-substituted thiazoles.

Aryl means phenyl, naphthyl, or other aromatic groups, including mono- or bicyclic, which may be unsubstituted or substituted, especially monosubstituted by F, Cl, Br, I, CF₃, OH, OR, or R, wherein R is lower alkyl.

Some of the above novel compounds may be prepared in accordance with well-known procedures for preparing peptides from their constituent amino acids. Other of the novel compounds of the present invention are prepared by a step-wise procedure or by a fragment coupling procedure depending upon the particular final product desired.

The following schemes illustrate novel methods of preparing certain compounds of the present invention.

Scheme I

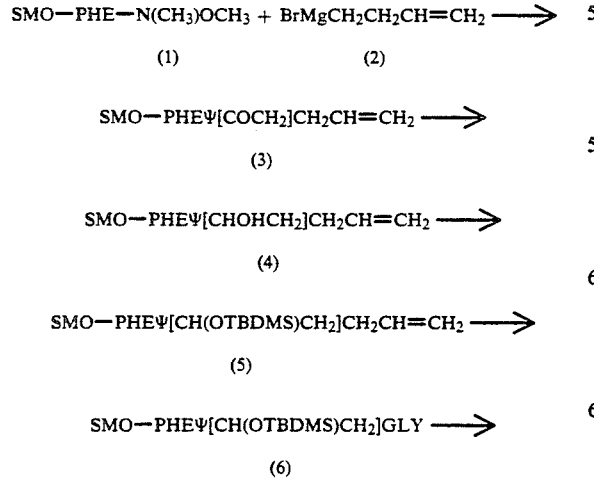

-continued
Scheme I

SMO—PHEΨ[CH(OTBDMS)CH₂]GLY—CAD ⟶

(7)

SMO—PHEΨ[CHOHCH₂]GLY—CAD (8)

According to Scheme I above, the O,N-dimethyl amide of SMO-PHE (1) is reacted with the Grignard reagent (2) prepared from 4-bromo-1-propene to give the ketomethylene isostere (3). The reaction takes place in an inert solvent such as Et₂O or THF at temperatures ranging from −40° to 25°.

Reduction gives the hydroxyethylene isostere (4). This reaction can be carried out with reducing agents such as LiBH₄, NaBH₄, KBH₄, or LiAlH₄ in an inert solvent such as Et₂O, or THF. For NaBH₄ or KBH₄, the reaction can also be carried out in MeOH or aqueous MeOH. In addition to the reduction, selection of a specific reducing agent mentioned above leads to different ratios of diastereomers formed in the reduction. Thus, one can select the reducing agent to give higher ratios of the desired diastereomer.

Protection of the hydroxyl group with t-butyldimethylsilyl chloride gives (5). This reaction is carried out in DMF using imidazole as the base. The reaction is carried out at room temperature for 12 to 40 hours.

Oxidation of the double bond gives (6). This reaction is carried out in aqueous acetone using RuO₂·XH₂O and NaIO₄ at 0° to 25° for one to four hours.

Compound (7) is prepared using standard peptide coupling methods. The preferred method is using DCC in the presence of HOBT in an inert solvent such as CH₂Cl₂, DMF, or THF. The reaction is carried out at 0° to 25° for 8 to 40 hours.

Removal of the protecting group to give compound (8) is carried out using tetrabutylammonium fluoride. This reaction is carried out in THF at room temperature for periods of 4 to 12 hours.

It will be evident to one skilled in the art that this series of reactions can be carried out with other compounds that contain the fragment Ψ[CHOHCH₂]CH₂CH=CH₂.

Scheme II

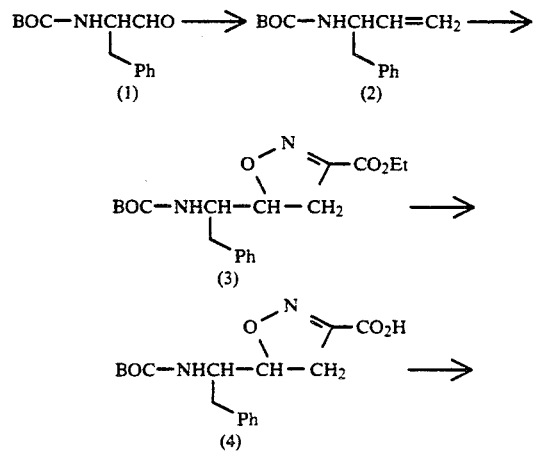

-continued
Scheme II

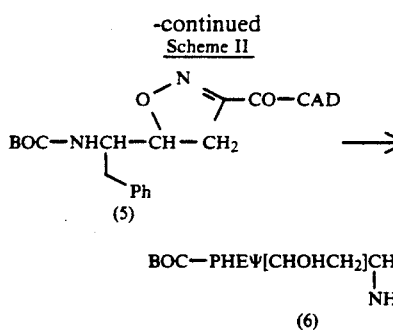

BOC—PHEΨ[CHOHCH$_2$]CHCO—CAD
                              |
                             NH$_2$
(6)

According to Scheme II above, the aldehyde (1) is reacted with methyltriphenylphosphonium bromide in an inert solvent such as THF using a base such as n-butyl lithium. The reaction can be carried out from −80° to 0° for two to 24 hours and leads to (2).

When (2) is treated with ethyl chlorooximinoacetate in an inert solvent such as Et$_2$O or THF and then treated slowly via a syringe pump with an organic base such as Et$_3$N over a period of 8 to 24 hours there is obtained (3).

Hydrolysis of (3) to give (4) can be carried out with alkali metal bases such as NaOH, KOH, or LiOH in aqueous MeOH, EtOH, or acetone at room temperature for periods of 1 to 4 hours.

Standard peptide coupling methods can be used to prepare (5). The preferred method is using DCC in the presence of HOBT in an inert solvent such as CH$_2$Cl$_2$, THF, or DMF at room temperature for 12 to 40 hours.

Catalytic reduction of (5) gives (6). This reaction can be carried out using Raney nickel catalyst in the presence of boric acid and hydrogen gas. The preferred solvents are MeOH, EtOH, or 2-propanol. The reaction is carried out at 40 to 75 psi for 2 to 8 hours.

The effectiveness of the aforementioned compounds is determined by a test for in vitro renin inhibitory activity. This activity is determined by a standard radioimmunoassay for angiotensin I. In this assay the enzyme, renin, incubated for 2 hours at 37° in the presence of a substrate, angiotensinogen, generates the product, angiotensin I. Test compounds are added to the incubation mixture. Relative activity is reported as the percent inhibition at the specified molar concentration or as the IC$_{50}$, which is the molar concentration of test compound causing a 50% inhibition of the renin activity.

TABLE II

| Compound | In Vitro Activity |
|---|---|
| SMO—PHEΨ[CHOHCH=CHCO]CAD | 2.5 × 10$^{-8}$* |
| BOC—PHEΨ[CH=CH]GLY—CAD | 1% @ 3 × 10$^{-8}$ |
| BOC—PHEΨ[CH——CH]GLY—CAD (epoxide O) | 21% @ 1 × 10$^{-8}$ |
| SMO—PHEΨ[COCH$_2$]GLY—CAD | 8.7 × 10$^{-8}$* |
| SMO—PHEΨ[CHOHCH$_2$]GLY—CAD (Isomer A) | 2.3 × 10$^{-9}$* |
| SMO—PHEΨ[CHOHCH$_2$]GLY—CAD (Isomer B) | 1.7 × 10$^{-8}$* |
| Z—PHEΨ[COCH$_2$]GLY—CAD | 1% @ 1 × 10$^{-8}$ |
| Z—PHEΨ[CHOHCH$_2$]GLY—CAD (Mixture of Diastereomers) | 2.4 × 10$^{-7}$* |
| Z—PHEΨ[CHOHCH$_2$]GLY—CAD (Slow Eluting Diastereomer) | 2.0 × 10$^{-7}$* |
| PHEΨ[CHOHCH$_2$]GLY—CAD | 28% @ 1 × 10$^{-6}$ |
| BOC—PHEΨ[CHOHCH$_2$]GLY—CAD (Mixture of Diastereomers) | 3.0 × 10$^{-8}$* |
| BOC—PHEΨ[CHOHCH$_2$]GLY—CAD (Slow Eluting Diastereomer) | 1.5 × 10$^{-8}$* |
| SMO—PHEΨ[CH$_2$NH]GLY—CAD | 2.6 × 10$^{-6}$* |
| BOC—PHEΨ[CHOHCH$_2$]CHCO—CAD, NH$_2$ (Isomer A) | 45% @ 10$^{-6}$ |
| BOC—PHEΨ[CHOHCH$_2$]CHCO—CAD, NH$_2$ (Isomer B) | 26% @ 10$^{-6}$ |

*IC$_{50}$

As can be seen from the above table, compounds of the present invention have a significant effect on the activity of renin and thus are useful for the treatment of hypertension, hyperaldosteronism, glaucoma, and congestive heart failure. They are also useful as agents for treatment of diseases caused by HTLV-I, II, III viruses.

The compounds of the instant invention, when tested by measuring the effect on intraocular pressure in rabbits as described by Tinjum, A. M., Acta Ophthamologica, 50, 677 (1972), are expected to exhibit antiglaucoma activity.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, favoring agents, solubilizers, lubricants, suspending agents, binders, or tablet disintegrating agents; it can also be encapsulating material. In powders, the carrier is a finely divided active compound. In the tablet the active compound is mixed with carrier having the necessary binding properties in suitable proportions and compacted in the shape and size desired. The powder and tablets preferably contain from 5 to 10 to about 70 percent of the active ingredient. Suitable solid carriers are magnesium carbonate, magnesium stearate, talc, sugar, tragacanth, methylcellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

The compounds of the present invention may be administered orally, buccally, parenterally, by inhalation spray, rectally, or topically in dosage unit formulations containing conventional nontoxic pharmaceutically acceptable carriers, adjuvants and vehicles as desired. The term parenteral as used herein includes subcutaneous injections, intravenous, intramuscular, intrasternal injection, or infusion techniques.

For preparing suppositories, a low melting wax such as a mixture of fatty acid glycerides or cocoa butter is first melted, and the active ingredient is dispersed homogeneously therein by stirring. The molten homogeneous mixture is then poured into convenient sized molds, allowed to cool, and thereby solidify.

Liquid form preparations include solutions, suspensions, and emulsions. As an example may be mentioned water or water/propylene glycol solutions for parenteral injection. Liquid preparations can also be formulated in solution in aqueous polyethylene glycol solution. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dosage form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerin, propylene glycol, and the like, as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampules. The unit dosage form can also be a capsule, cachet, or tablet itself, or it can be the appropriate number of any of these in packaged form.

The quantity of active compound in a unit dose of preparation may be varied or adjusted from 1 mg to 500 mg, preferably 5 to 100 mg according to the particular application and the potency of the active ingredient. The composition can, if desired, also contain other compatible therapeutic agents.

In therapeutic use as renin inhibitors, the mammalian dosage range for a 70 kg subject is from 1 to 1500 mg/kg of body weight per day or preferably 25 to 750 mg/kg of body weight per day optionally in divided portions. The dosages, however, may be varied depending upon the requirements of the patient, the severity of the condition being treated, and the compound being employed. Determination of the proper dosage for a particular situation is within the skill of the art. Generally, treatment is initiated with small dosages which are less than the optimum dose of the compound. Thereafter the dosage is increased by small increments until the optimum effect under the circumstances is reached. For convenience, the total daily dosage may be divided and administered in portions during the day, if desired.

In therapeutic use as an antiglaucoma agent, the compound may also be administered as a topical corneal application of a solution containing the compound in amounts as known to one skilled in the treatment.

The present invention includes combinations of novel renin-inhibiting compounds of formula I with one or more antihypertensive agents selected from the group consisting of diuretics, α- and/or β-adrenergic blocking agents, calcium channel blocking agents, central nervous system-acting agents, adrenergic neuron blocking agents, vasodilators, angiotensin converting enzyme inhibitors, and other antihypertensive agents.

The following examples are provided to enable one skilled in the art to practice the present invention. These examples are not intended in any way to limit the scope of the invention but are illustrative thereof.

EXAMPLE 1

SMO-PHEΨ[CHOHCH=CHCO]CAD

A solution of 740 mg (2.0 mmole) of

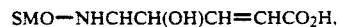

270 mg (2.0 mmole) of HOBT, and 560 mg (2.0 mmole) of CAD HC (EP-229,667) in 15 ml DMF was cooled in ice and 0.3 ml (2.0 mmole) of Et₃N added, followed by a solution of 420 mg (2.0 mmole) of DCC in 5 ml DMF. After stirring for 15 minutes at 0°, the mixture was allowed to stir at room temperature overnight. The mixture was filtered and the DMF removed under high vacuum. The residue was taken up in EtOAc, filtered, and washed with 1 N HCl, H₂O, saturated NaHCO₃, and saturated NaCl. Drying over MgSO₄ and removal of the solvent under reduced pressure gave 1.1 g of the crude product as a tan solid. Chromatography on silica gel, eluting with CHCl₃/MeOH (96/4) gave the product. Recrystallization from EtOAc/hexane gave 487 mg of the product as a white solid. The structure was confirmed by mass spectroscopy.

Calcd. for C$_{30}$H$_{49}$N$_3$O$_7$S (MW 595.72): C, 60.48; H, 8.29; N, 7.05.

Found: C, 61.06; H, 8.36; N, 6.73.

EXAMPLE 2

BOC-PHEΨ[E-CH=CH]GLY-CAD

A solution of 1.55 g (5.1 mmole) of [S-(E)]-5-[[(1,1-dimethylethoxy)carbonyl]amino]-6- phenyl-3-hexenoic acid (J. Chem. Soc. 799 (1980)), 686 mg (5.1 mmole) of HOBT, and 1.43 g (5.1 mmole) of CAD·HCl in 25 ml DMF was cooled in ice and treated with a solution of 1.05 g (5.1 mmole) of DCC in 10 ml DMF followed by 0.71 ml (5.1 mmole) of Et₃N. After 15 minutes at 0°, the mixture was allowed to stir at room temperature overnight. The mixture was filtered and the solvent removed under high vacuum. The residue was taken up in EtOAc, filtered, and washed with 1N HCl, H₂O, saturated NaHCO₃, and saturated NaCl. Drying over MgSO₄ and removal of the solvent under reduced pressure left 2.7 g of the crude product. Chromatography on silica gel, eluting with CHCl₃/MeOH (98/2) gave 2.4 g of the product as a white solid. The structure was confirmed by NMR and mass spectroscopy.

Calcd. for C$_{31}$H$_{50}$N$_2$O$_5$·0.1CHCl$_3$ (MW 542.66): C, 68.83; H, 9.31; N, 5.16.

Found: C, 68.99; H, 9.35; N, 4.96.

EXAMPLE 3

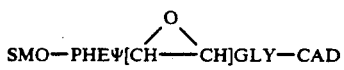
SMO—PHEΨ[CH——CH]GLY—CAD

A solution of 0.5 g (0.94 mmole) of SMO-PHEΨ[E-CH=CH]GLY-CAD in 10 ml $CH_2Cl_2$ was treated with 291 mg (1.43 mmole) of m-chloroperbenzoic acid and allowed to stir at room temperature for three days. The solvent was removed under reduced pressure and the residue taken up in EtOAc and washed with 5% $NaHSO_3$, $H_2O$, saturated $NaHCO_3$, and saturated NaCl. Drying over $MgSO_4$ and removal of the solvent under reduced pressure gave 490 mg of the crude product. Chromatography on silica gel, eluting with $CHCl_3$/MeOH (98/2) gave 220 mg of the product as a white foam. The structure was confirmed by NMR and mass spectroscopy.

Calcd. for $C_{31}H_{50}N_2O_6 \cdot 0.15$ $CHCl_3$ (MW 564.63): C, 66.26; H, 8.95; N, 4.96.

Found: C, 66.12; H, 8.69; N, 4.67.

EXAMPLE 4

SMO-PHEΨ[COCH$_2$]GLY-CAD

A solution of 1.6 g (4.32 mmole) of SMO-PHEΨ[COCH$_2$]GLY and 0.6 g (4.4 mmole) of HOBT in 75 ml $CH_2Cl_2$ and 5 ml DMF was cooled in ice and treated with 0.91 g (4.4 mmole) of DCC, followed by a solution of 1.05 g (4.32 mmole) of CAD in 25 ml $CH_2Cl_2$/DMF (1/1). After stirring at room temperature overnight, the mixture was filtered and the solvent removed under reduced pressure. The residue was taken up in $Et_2O$ and washed with 1N citric acid, saturated NaCl, saturated $NaHCO_3$, and saturated NaCl. After drying over $MgSO_4$, the product was precipitated by the addition of hexane to the $Et_2O$ solution. There was obtained 1.55 g of the product. The structure was confirmed by NMR and mass spectroscopy.

Calcd. for $C_{30}H_{49}$ $N_3O_7S \cdot 0.3$ $H_2O$ (MW 601.21): C, 59.93; H, 8.31; N, 6.99.

Found: C, 59.81; H, 8.20; N, 6.91.

EXAMPLE 5

SMO-PHEΨ[CHOHCH$_2$]GLY-CAD (Isomer A)

A solution of 2.58 g (3.62 mmole) of SMO-PHEΨ[CH(OTBDMS)CH$_2$]GLY-CAD, Isomer A, in 70 ml of a 1M solution of tetrabutylammonium fluoride in THF was stirred at room temperature for six hours. The solvent was removed under reduced pressure to give an oil. This was taken up in EtOAc and washed three times with 1N HCl, three times with saturated $NaHCO_3$, then with saturated NaCl. Drying over $MgSO_4$ and removal of the solvent under reduced pressure gave 2.13 g of the crude product. Recrystallization from $CH_2Cl_2$/$Et_2O$ gave 1.59 g of the product as a white solid. The structure was confirmed by NMR and mass spectroscopy.

Calcd. for $C_{30}H_{51}N_3O_7S \cdot 0.5$ $H_2O$ (MW 606.83): C, 59.38; H, 8.64; N, 6.92.

Found: C, 59.25; H, 8.48; N, 6.89.

EXAMPLE 6

SMO-PHEΨ[CHOHCH$_2$]GLY-CAD (Isomer B)

In a manner similar to that of Example 5, 2.55 g (3.58 mmole) of SMO-PHEΨ[CH(OTBDMS)CH$_2$]GLY-CAD, Isomer B, gave 0.75 g of the product as a pale yellow solid. The structure was confirmed by NMR and mass spectroscopy.

Calcd. for $C_{30}H_{51}N_3O_7S \cdot 0.25H_2O$ (MW 602.32): C, 59.82; H, 8.62; N, 6.98.

Found: C, 59.85; H, 8.49; N, 6.92.

EXAMPLE 7

SMO-PHEΨ[CHOHCH$_2$]GLY-CAD (Mixture of Diastereomers)

A solution of 1.1 g (2.45 mmole) of PHEΨ[CHOHCH$_2$GLY-CAD (mixture of diastereomers, Example 11) and 0.47 g (2.7 mmole) of morpholinosulfamyl chloride (prepared according to the method of R. Wegler and K. Bodenbenner, Ann 624, 25 (1959)) in 50 ml DMF was treated with 0.38 ml (2.7 mmole) of $Et_3N$ and stirred at room temperature for four days. The solvent was removed under reduced pressure and the residue suspended in EtOAc. This was washed with 1 N citric acid, saturated $NaHCO_3$, and saturated NaCl. Drying over $MgSO_4$ and removal of the solvent under reduced pressure gave 1.51 g of the crude product. Chromatography on silica gel, eluting with a gradient of 2%–15% MeOH in $CHCl_3$ gave the product. Trituration with $Et_2O$ gave 0.76 g of the product as a white solid. The structure was confirmed by NMR and mass spectroscopy.

Calcd. for $C_{30}H_{51}N_3O_7S \cdot 0.25$ $H_2O$ (MW 602.32): C, 59.82; H, 8.62; N, 6.97.

Found: C, 59.71; H, 8.88; N, 6.89.

EXAMPLE 8

Z-PHEΨ[COCH$_2$]GLY-CAD

A solution of 10.1 g (28.4 mmole) of Z-PHEΨ[COCH$_2$]GLY and 3.92 g (28.9 mmole) of HOBT in 150 ml $CH_2Cl_2$ and 60 ml DMF was cooled in ice and 5.98 g (28.9 mmole) of DCC added, followed by a solution of 7.95 g (28.4 mmole) of CAD·HCl and 4.04 ml (28.9 mmole) of $Et_2N$ in 150 ml of cold $CH_2Cl_2$. After stirring at room temperature overnight, the mixture was filtered, and the filtrate evaporated to an oil. This was taken up in $Et_2O$ and washed with 1N citric acid, saturated NaCl, saturated $NaHCO_3$, and saturated NaCl. Drying over $MgSO_4$ and removal of the solvent under reduced pressure left a solid. Recrystallization from $CHCl_3/Et_2O$ gave 11.03 g of the product. The structure was confirmed by NMR and mass spectroscopy.

Calcd. for $C_{34}H_{48}N_2O_6$ (MW 580.77): C, 70.32; H, 8.33; N, 4.82.

Found: C, 70.23; H, 8.43; N, 4.82.

EXAMPLE 9

Z-PHEΨ[CHOHCH$_2$]GLY-CAD (Mixture of Diastereomers)

A suspension of 9.08 g (15.63 mmole) of Z-PHEΨ[COCH$_2$GLY-CAD (Example 8) in 250 ml absolute EtOH was warmed to 40° to effect solution, and 25 ml of $H_2O$ was then added, followed by 3.37 g (62.5 mmole) of $KBH_4$. After stirring at room temperature for 1.5 hours, the suspension was filtered, and 25 ml acetone added, followed by 5 ml of HOAc. The solvent was removed under reduced pressure and the residue mixed with 200 ml of $H_2O$, giving a solid. This was collected, then suspended in warm $CHCl_3$. A solid was filtered off, and the filtrate washed with 1N citric acid, saturated NaCl, saturated $NaHCO_3$, and saturated NaCl. Drying over $MgSO_4$ and removal of the solvent under reduced pressure left a solid. Trituration with Et$_2$O gave 4.11 g of the product as a white solid. Thin layer showed this to be a mixture of fast and slow running diastereomers. The structure was confirmed by NMR and mass spectroscopy.

Calcd. for C$_{34}$H$_{50}$N$_2$O$_6$ (MW 582.79): C, 70.07; H, 8.65; N, 4.81.
Found: C, 69.90; H, 8.77; N, 4.93.

EXAMPLE 10

Z-PHEΨ[CHOHCH$_2$]GLY-CAD (Slow Isomer)

The CHCl$_2$-insoluble solid from Example 9 was dissolved in a large volume of hot CHCl$_3$, and while hot, washed with 1N citric acid, saturated NaCl, saturated NaHCO$_3$, and saturated NaCl. The hot solution was dried over MgSO$_4$ and then concentrated to a small volume. Addition of Et$_2$O gave 3.13 g of the product as a white solid. Thin layer showed this to be the slow running diastereomer. The structure was confirmed by NMR and mass spectroscopy.

Calcd. for C$_{34}$H$_{50}$N$_2$O$_6$ (MW 582.79): C, 70.07; H, 8.65; N, 4.81.
Found: C, 70.18; H, 9.00; N, 4.63.

EXAMPLE 11

PHEΨ[CHOHCH$_2$]GLY-CAD (Mixture of Diastereomers)

A solution of 3.72 g (6.38 mmole) of Z-PHEΨ[CHOHCH$_2$]GLY-CAD (mixture of diastereomers, Example 9) in 100 ml MeOH was treated with 370 mg of 20% Pd/C and purged with hydrogen for three hours. The suspension was filtered and the solvent removed under reduced pressure, leaving 2.77 g of the crude product. Chromatography on silica gel, eluting with a gradient of 0%–5% MeOH in CHCl$_3$ gave 2.61 g of the product as a solid. The structure was confirmed by NMR and mass spectroscopy.

Calcd. for C$_{26}$H$_{44}$N$_2$O$_4$ (MW 448.65): C, 69.60; H, 9.88; N, 6.24.
Found: C, 69.22; H, 9.93; N, 6.13.

EXAMPLE 12

PHEΨ[CHOHCH$_2$]GLY-CAD (Slow Isomer)

A solution of 2.79 g (4.79 mmole) of Z-PHEΨ[CHOHCH$_2$GLY-CAD (slow isomer, Example 10) in 100 ml MeOH was treated with 350 mg of 20% Pd/C and purged with hydrogen for three hours. The suspension was filtered and the solvent removed under reduced pressure, leaving 2.09 g of the product as a white foam. The structure was confirmed by NMR and mass spectroscopy.

Calcd. for C$_{26}$H$_{44}$N$_2$O$_4$·0.5MeOH (MW 464.67): C, 68.49; H, 9.98; N, 6.03.
Found: C, 68.61; H, 9.86; N, 5.93.

EXAMPLE 13

BOC-PHEΨ[CHOHCH$_2$]GLY-CAD (Mixture of Diastereomers)

A solution of 1.25 g (2.79 mmole) of PHEΨ[CHOHCH$_2$]GLY-CAD (mixture of diastereomers, Example 11) and 0.67 g (3.07 mmole) of di-t-butyldicarbonate in 50 ml THF was stirred at room temperature overnight. The solvent was removed under reduced pressure and the residue triturated with Et$_2$O to give 1.15 g of crude product. Chromatography on silica gel, eluting with CHCl$_3$/MeOH (9/1) gave 0.93 g of the product as a white solid. The structure was confirmed by NMR and mass spectroscopy.

Calcd. for C$_{31}$H$_{52}$N$_2$O$_6$·0.05 CHCl$_3$(MW 555.54): C, 67.13; H, 9.44; N, 5.04.
Found: C, 67.38; H, 9.57; N, 4.96.

EXAMPLE 14

BOC-PHEΨ[CHOHCH$_2$]GLY-CAD (Slow Isomer)

In a manner similar to that described for Example 13, 1.25 g (2.79 mmole) of PHEΨ[CHOHCH$_2$]GLY-CAD (slow isomer, Example 12) gave 0.84 g of product as a white solid. The structure was confirmed by NMR and mass spectroscopy.

Calcd. for C$_{31}$H$_{52}$N$_2$O$_6$ (MW 548.77): C, 67.85; H, 9.55; N, 5.10.
Found: C, 67.45; H, 9.56; N, 4.94.

EXAMPLE 15

SMO-PHEΨ[CH$_2$NH]GLY-CAD

A solution of 3.1 g (10.4 mmole) of SMO-PHE[CHO] and 3.15 g (10.5 mmole) of GLY-CAD in 250 ml absolute EtOH was treated with 16 g of activated 3A molecular sieves followed by 0.72 g (11.5 mmole) of NaCNBH$_3$ and a trace of bromocresol green. The blue solution was gradually acidified with HCl gas in EtOH over one hour, until the solution remained green. After stirring at room temperature for three days the mixture was filtered and evaporated to a foam. This was taken up in EtOAc and washed with 1N HCl, saturated NaCl, saturated NaHCO$_3$, and saturated NaCl. Drying over MgSO$_4$ and removal of the solvent under reduced pressure gave 5.77 g of the crude product. Chromatography on silica gel, eluting with EtOAc/CHCl$_3$ (1/1) gave 3.0 g of a white foam. This was rechromatographed on silica gel, eluting with a gradient of 0%–3% MeOH in CHCl$_3$ to give 2.81 g of the product as a white foam. The structure was confirmed by NMR and mass spectroscopy.

Calcd. for C$_{29}$H$_{50}$N$_4$O$_6$S·0.05CHCl$_3$·0.25H$_2$O (MW 593.28): C, 58.81; H, 8.59; N, 9.44.
Found: C, 58.71; H, 8.72; N, 9.33.

EXAMPLES 16 AND 17

BOC-PHEΨ[CHOHCH$_2$]CH(NH$_2$)CO-CAD (Isomers A and B)

To a solution of 3.82 g (6.82 mmole) of

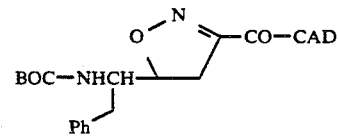

and 0.84 g (13.65 mmole) of boric acid in 250 ml of 10% aqueous MeOH was added 0.5 g of Raney nickel and the suspension shaken under an atmosphere of hydrogen at 53 psi for four hours. The catalyst was removed by filtration through Celite and the filtrate concentrated under reduced pressure to a volume of approximately 50 ml. The concentrated filtrate was diluted with ethyl acetate and extracted three times with brine. The organic phase was dried over MgSO$_4$, filtered, and the solvent removed under reduced pressure to give 3.84 g of a diastereomeric mixture of the products. These were separated by flash chromatography using a gradient of 2%–10% MeOH in CH₂C₂. After the initial elution of BOC-PHEΨ[CHOHCH₂]COCO-CAD, continued elution gave 1.02 g of the product, Isomer A, which was purified by recrystallization from Et₂O. The structure was confirmed by NMR and mass spectroscopy.

Calcd. for C₃₁H₅₃N₃O₆ (MW 563.77): C, 66.04; H, 9.48; N, 7.45.

Found: C, 65.83; H, 9.27; N, 7.21.

Continued elution from the column gave 0.79 g of the product, Isomer B, which was purified by recrystallization from EtOAc/hexane. The structure was confirmed by NMR and mass spectroscopy.

Calcd. for C₃₁H₅₃N₃O₆ (MW 563.77): C, 66.04; H, 9.48; N, 7.45.

Found: C, 66.39; H, 9.43; N, 7.27.

EXAMPLE 18

SMO-PHEΨ[CH(NH₂)CH₂]GLY-CAD·HCl

A solution of 0.99 g (1.66 mmole) of SMO-PHEΨ[COCH₂]GLY-CAD, (Example 4) and 9.7 g (0.126 mole) of NH<OAc in 30 ml MeOH was treated with 20 g of activated 3A molecular sieves. This was then treated with 0.32 g (3.32 mmole) of NaCNBH₃ and the mixture left stirring at room temperature overnight. The mixture was then filtered and the solvent removed under reduced pressure. The residue was taken up in EtOAc and washed with H₂O, 1 N citric acid, saturated NaCl, saturated NaHCO₃, and saturated NaCl. Drying over MgSO₄ and removal of the solvent under reduced pressure left 0.68 g of the crude product. This was taken up in EtOAc/Et₂O, filtered, and the filtrate treated with HCl gas. The precipitated solid was collected and washed with Et₂O to give 0.59 g of the product as a yellow solid. The structure was confirmed by NMR and mass spectroscopy.

Calcd. for C₃₀H₅₂N₄O₆S·HCl (MW 633.21): C, 56.90; H, 8.44; N, 8.85.

Found: C, 56.58; H, 8.19; N, 8.50

INTERMEDIATES FOR EXAMPLE 1

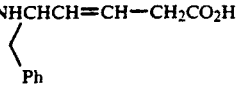

Under nitrogen, a suspension of 50.9 g (0.11 mole) of 1-trimethysilylpropyne-3-triphenylphosphonium bromide (J. Chem. Soc. Perkin I, 307 (1982)) in 500 ml THF was cooled to −80° and 70 ml (0.11 mole) of a 1.6 M solution of n-butyl lithium in hexane was added slowly via a syringe. The dark red-brown suspension was stirred at −80° for 1.5 hours after the addition was complete. This was then treated dropwise with a solution of 16.7 g (0.056 mole) of SMO-PHE[CHO] in 500 ml THF. After one hour at −80°, the mixture was left at room temperature overnight. The solvent was removed under reduced pressure and the residue taken up in EtOAc and washed with 1 N citric acid, H₂O, saturated NaHCO₃, and saturated NaCl. Drying over MgSO₄ and removal of the solvent under reduced pressure left 44.3 g of a dark oil. Chromatography on silica gel, eluting with CHCl₃ gave 11.6 g of product. Recrystallization from Et₂O/hexane gave 7.8 g of pure product, mp 128°–130°. The NMR confirmed this as the E-isomer (J=16 H₂).

SMO—NHCHCH=CH—CH₂CO₂H
\
Ph

Under nitrogen, 70 ml (0.07 mole) of a 1 M solution of BH₃ in THF was cooled in ice and treated dropwise with a solution of 14.1 ml (0.139 mole) of cyclohexene in 150 ml THF. After the addition was complete, the mixture was stirred at 0° for one hour. The suspension was then treated with a solution of 7.78 g (0.02 mole) of SMO—NHCHCH=CH—C≡C—SiMe₃
\
Ph in 25 ml THF. After stirring at 0° for one hour, the mixture was treated dropwise with 26 ml MeOH, 36 ml 2 N NaOH, and then with 24 ml of 30% H₂O₂, keeping the temperature below 18°. After stirring at 0° for 20 minutes, the mixture was allowed to stir at room temperature for one hour. This was poured into 500 m H₂O containing 27 ml of 2 N NaOH. After extracting three times with Et₂O, the pH was brought to 2.0 with di. HCl, and the solution extracted three times with Et₂O. The combined Et₂O phases were washed with saturated NaCl, dried over MgSO₄, and the solvent removed under reduced pressure leaving 6.3 g of the product or a viscous oil. The structure was confirmed by NMR and mass spectroscopy.

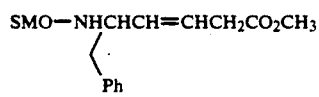

A solution of 5.3 g (0.015 mole) of

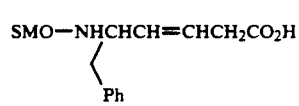

in 40 ml THF was cooled in ice and 2.76 g (0.017 mole) of CDI added. The solution was stirred at room temperature for 0.5 hours, diluted with 150 ml MeOH, and stirred at room temperature overnight. The solvent was removed under reduced pressure and the residue taken up in Et₂O, washed two times with 1 N HCl, H₂O, two times with saturated NaHCO₃, and then with saturated NaCl. Drying over MgSO₄ and removal of the solvent under reduced pressure left 4.37 g of a yellow solid. Chromatography on silica gel, eluting with CHCl₃/MeOH (98/2) gave 3.8 g of an oil which solidified on standing. Recrystallization from MeOH/H₂O gave 3.37 g of the product as a white solid, mp 80°–81°. The structure was confirmed by NMR and mass spectroscopy.

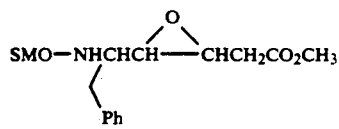

A solution of 3.37 g (9.1 mmole) of

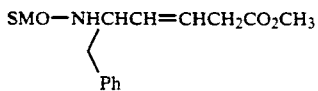

in 40 ml CH$_2$C$_2$ was treated with 3.0 g (13.7 mmole) of m-chloroperbenzoic acid and stirred at room temperature overnight. The mixture was filtered and the solvent removed under reduced pressure. The residue was taken up in EtOAc and washed twice with 5% Na$_2$SO$_3$, H$_2$O, saturated NaHCO$_3$, and then with saturated NaCl. Drying over MgSO$_4$ and removal of the solvent under reduced pressure left 3.36 g of the crude product. Since NMR showed some double bond still present, the material was resubjected to the oxidation conditions. Using the same workup as before gave 3.2 g of the crude product as an oil. Chromatography on silica gel, eluting with CHCl$_3$/MeOH (99/1) gave 1.53 g of the product as an oil. The material was used directly in the next step.

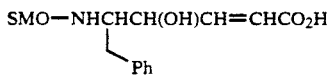

A solution of 1.53 g (4.0 mmole) of

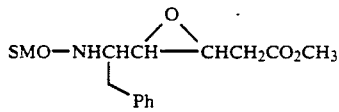

in 20 ml MeOH was treated with 15 ml (15 mmole) of 1 N NaOH and stirred at room temperature for two hours. The solvent was removed under reduced pressure and the residue taken up in H$_2$O and washed twice with Et$_2$O. The pH was brought to 2.1 with dilute HCl and the solution extracted twice with CHCl$_3$. The CHCl$_3$ was washed with saturated NaCl, dried over MgSO$_4$, and the solvent removed under reduced pressure, leaving 0.75 g of the product as a golden foam. The structure was confirmed by NMR and mass spectroscopy.

INTERMEDIATE FOR EXAMPLE 4

SMO-PHEΨ[COCH$_2$]GLY

To a solution of 2.33 g (6.6 mmole) of SMO-PHEΨ[COCH$_2$]CH$_2$CH=CH$_2$ in 140 ml acetone was added a solution of 10.6 g (49.6 mmole) of NaIO$_4$ and 110 mg of RuO$_2$·XH$_2$O in 60 ml H$_2$O. After stirring at room temperature for two hours, 20 ml of 2-propanol was added, and the mixture filtered through Celite. The filtrate was concentrated to an aqueous suspension. This was saturated with solid NaHCO$_3$, filtered, and washed with CHCl$_3$. The pH was then adjusted to 1.0 with conc. HCl, and the mixture extracted with CHCl$_3$. The CHCl$_3$ extract was washed with a 4% solution of Na$_2$SO$_3$ which had been adjusted to pH 2, then with saturated NaCl. After drying over MgSO$_4$, the solvent was removed under reduced pressure to give 1.81 g of the product as a white foam. The structure was confirmed by NMR and mass spectroscopy.

INTERMEDIATES FOR EXAMPLES 4–6

SMO-PHEΨ[COCH$_2$]CH$_2$CH=CH$_2$

Under nitrogen, a Grignard solution prepared from 5.44 g (224 mmole) of Mg turnings and 22.7 ml (224 mmole) of 4-bromo-1-butene in 350 ml THF was heated to reflux, then cooled to −5° and treated with a suspension of 20.0 g (55.9 mmole) of SMO-PHE-N(CH$_3$)OCH$_3$ in 135 ml THF. After stirring at room temperature overnight, the mixture was evaporated to an oil. The oil was poured into a cold, saturated solution of NH$_4$Cl and extracted with EtOAc. The EtOAc was washed with 1 N citric acid, saturated NaCl, saturated NaHCO$_3$, and saturated NaCl. Drying over MgSO$_4$ and removal of the solvent under reduced pressure gave the crude product as an oil. Chromatography on silica gel, eluting with hexane/EtOAc (70/30) gave 16.9 g of the product as an oil. The structure was confirmed by NMR and mass spectroscopy.

SMO-PHEΨ[CHOHCH$_2$]CH$_2$CH=CH$_2$

A solution of 6.35 g (18.0 mmole) of SMO-PHEΨ[COCH$_2$]CH$_2$CH=CH$_2$ in 200 ml of absolute EtOH was treated with 3.89 g (72.0 mmole) of KBH$_4$ followed by 20 ml H$_2$O. After stirring at room temperature for 2.5 hours, 100 ml of acetone was added and the mixture stirred for 15 minutes. The suspension was filtered and the filtrate evaporated to an oil which solidified. There was obtained 6.04 g of the product. The structure was confirmed by NMR and mass spectroscopy.

SMO-PHEΨ[CH(OTBDMS)CH$_2$]CH$_2$CH=CH$_2$

A solution of 5.95 g (16.8 mmole) of SMO-PHEΨ[CHOHCH$_2$]CH$_2$CH=CH$_2$ in 100 ml THF was treated with 1.48 g (22 mmole) of imidazole and 3.29 g (22 mmole) of t-butyldimethysilyl chloride and the mixture stirred at room temperature for two days. An additional 0.8 g (11.8 mmole) of imidazole and 1.77 g (11.7 mmole) of t-butyldimethylsilyl chloride was then added and the mixture stirred overnight. The solvent was removed under reduced pressure and the residue suspended in EtOAc/Et$_2$O (1/1) and washed with H$_2$O, 1 N citric acid, saturated NaCl, saturated NaHCO$_3$, and saturated NaCl. Drying over MgSO$_4$ and removal of the solvent under reduced pressure gave the crude product as a mixture of diastereomers. Chromatography on silica gel, eluting with a gradient of 0%–20% EtOAc in hexane gave 3.34 g of the faster eluting diastereomer as a glass. The structure was confirmed by NMR and mass spectroscopy.

Continued elution from the column gave 2.86 g of the slower eluting diastereomer as a glass. The structure was confirmed by NMR and mass spectroscopy.

SMO-PHEΨ[CH(OTBDMS)CH$_2$]GLY (Isomer A)

A solution of 3.04 g (6.49 mmole) of SMO-PHEΨ[CH(OTBDMS)CH$_2$]CH$_2$CH=CH$_2$ (fast isomer) in 140 ml acetone was treated with a solution of 10.4 g (48.77 mmole) of NaIO$_4$ and 100 mg of RuO$_2$·XH$_2$O in 60 ml H$_2$O and the mixture stirred at 15° for two hours. This was then treated with 30 ml of 2-propanol and the mixture filtered through Celite. The filtrate was concentrated to an aqueous suspension. This was saturated with solid NaHCO$_3$, filtered, and extracted with CHCl$_3$, which carried over the sodium salt. The CHCl$_3$ was extracted with a 4% solution of Na$_2$SO$_3$ which had been adjusted to pH 2, then with saturated NaCl. Drying over MgSO$_4$, and removal of the solvent under reduced pressure gave the crude product. This was taken up in Et$_2$O, filtered, and the solvent removed under reduced pressure to give 1.88 g of the product as a white foam. The structure was confirmed by NMR and mass spectroscopy.

SMO-PHEΨ[CH(OTBDMS)CH$_2$]GLY (Isomer B)

In a manner similar to that described for Isomer A, 2.77 g (5.91 mmole) of SMO-PHEΨ[CH(OTBDMS)CH$_2$]CH$_2$CH=CH$_2$ (slow isomer) gave 1.95 g of the product after recrystallization from hexane. The structure was confirmed by NMR and mass spectroscopy.

SMO-PHEΨCH(OTBDMS)CH$_2$]GLY-CAD (Isomer A)

A solution of 1.79 g (3.68 mmole) of SMO-PHEΨ[CH(OTBDMS)CH$_2$GLY, (Isomer A) and 0.51 g (3.79 mmole) of HOBT in 80 ml CH$_2$Cl$_2$ and 5 ml DMF was cooled in ice and treated with 0.78 g (3.79 mmole) of DCC, then with a solution of 0.9 g (3.68 mmole) of CAD in 25 ml of DMF/CH$_2$Cl$_2$ (80/20). After stirring at room temperature overnight, the mixture was filtered and the solvent removed under reduced pressure. The residue was taken up in EtOAc and washed with 1 N citric acid, saturated NaCl, saturated NaHCO$_3$, and saturated NaCl. Drying over MgSO$_4$ and removal of the solvent under reduced pressure left an oil. This was taken up in Et$_2$O, filtered to remove insolubles, and evaporated to give 2.7 g of the product as a white foam. The structure was confirmed by NMR and mass spectroscopy.

SMO-PHEΨ[CH(OTBDMS)CH$_2$]GLY-CAD (Isomer B)

In a manner similar to that described for Isomer A, 1.86 g (3.82 mmole) of SMO-PHEΨ[CH(OTBDMS)CH$_2$]GLY, (Isomer B) gave 2.76 g of the product as a white foam. The structure was confirmed by NMR and mass spectroscopy.

INTERMEDIATES FOR EXAMPLE 8

Z-PHEΨ[COCH$_2$]GLY[(CO$_2$H)$_2$]

A solution of 22.7 g (44.37 mmole) of Z-PHEΨ[COCH$_2$]GLY[(CO$_2$-t-Bu)$_2$], (U.S. Pat. No. 4,743,585), in 150 ml of CH$_2$Cl$_2$ was treated with 150 ml of TFA and stirred at room temperature for three hours. The solvent was removed under reduced pressure, and the residue taken up in CH$_2$Cl$_2$ and the solvent removed again. This process was then repeated giving a solid. This was taken up in Et$_2$O, washed with saturated NaCl, and then with saturated NaHCO$_3$. The NaHCO$_3$ solution was brought to pH 1 and extracted with Et$_2$O. The Et$_2$O phase was washed with saturated NaCl, dried over MgSO$_4$, and the solvent removed under reduced pressure, leaving 16.25 g of the product as a white foam. The structure was confirmed by NMR and mass spectroscopy.

Z-PHEΨ[COCH$_2$]GLY

A solution of 15.06 g (37.7 mmole) of Z-PHEΨ[COCH$_2$GLY[(CO$_2$H)$_2$] in 300 ml toluene was heated at reflux for five hours. The solvent was removed under reduced pressure and the residue taken up in Et$_2$O. This was washed with 1 N citric acid, saturated NaCl, and saturated NaHCO$_3$. The NaHCO$_3$ wash was brought to the Congo Red color change with conc. HCl, then extracted with Et$_2$O. The Et$_2$O was washed with saturated NaCl and dried over MgSO$_4$. Dilution with hexane caused a solid to precipitate. The mixture was concentrated under reduced pressure, and the solid collected and washed with hexane. There was obtained 10.33 g of the product as a white solid. The structure was confirmed by NMR and mass spectroscopy.

INTERMEDIATES FOR EXAMPLES 1 AND 15

SMO-PHE-N(CH$_3$)OCH$_3$

A solution of 8.0 g (25.4 mmole) of SMO-PHE in 100 ml of THF/CH$_2$Cl$_2$ (1/1) was cooled to −40° and 4.54 g (28 mmole) of carbonyldiimidazole added. The mixture was then kept at −5° for 1.5 hours. To this was added a solution of 2.73 g (28 mmole) of O,N-dimethylhydroxylamine, hydrochloride, and 3.23 ml (28 mmole) of N-methylpiperidine in 40 ml CH$_2$C$_2$. After stirring at room temperature overnight, the mixture was filtered and the filtrate evaporated. The residue was taken up in EtOAc and washed with 1 N citric acid, saturated NaCl, saturated NaHCO$_3$, and saturated NaCl. Drying over MgSO$_4$ and removal of the solvent under reduced pressure left 9.69 g of the crude product. Chromatography on silica gel, eluting with EtOAc/CHCl$_3$/MeOH (49/49/2) gave 7.56 g of the product as a syrup which solidified. The structure was confirmed by NMR and mass spectroscopy.

SMO-PHE[CHO]

A solution of 5.0 g (14.0 mmole) of SMO-PHE-N(CH$_3$)OCH$_3$ in 60 ml THF was cooled to −10° and 1.09 g (28.7 mole) of lithium aluminum hydride added rapidly in portions. After stirring at −20° for 20 minutes, a solution of 6.8 g KHSO$_4$ in 50 ml H$_2$O was added as rapidly as possible while controlling vigorous off-gassing. After adjusting the pH to 2, the mixture was extracted with EtOAc. The EtOAc was washed with 1 N HCl, then with saturated NaCl. Drying over MgSO$_4$ and removal of the solvent under reduced pressure gave a solid. This was triturated with Et$_2$O to give 3.3 g of the product as a white solid. The structure was confirmed by NMR.

INTERMEDIATES FOR EXAMPLE 15

Z-GLY-CAD

A solution of 2.09 g (10.0 mmole) of Z-GLY and 1.37 g (10.2 mmole) of HOBT in 40 ml CH$_2$Cl$_2$ and 6 ml DMF was cooled in ice and 2.1 g (10.2 mmole) of DCC added, followed by a solution of 2.79 g (10.0 mmole) of CAD·HCl and 1.42 ml (10.3 mmole) of Et$_3$N in 40 ml CH$_2$Cl$_2$. After stirring at room temperature overnight, the mixture was filtered and the solvent removed under reduced pressure. The residue was taken up in EtOAc and washed with 1 N citric acid, saturated NaCl, saturated NaHCO$_3$, and saturated NaCl. Drying over MgSO$_4$ and removal of the solvent under reduced pressure left 2.92 g of a solid. Two recrystallizations from EtOAc/Et$_2$O gave 2.63 g of the product as a white solid. The structure was confirmed by NMR and mass spectroscopy.

GLY-CAD

A solution of 9.4 g (21.6 mmole) of Z-GLY-CAD in 250 ml MeOH was treated with 0.8 g of 20% Pd/C and purged with hydrogen for three hours. The mixture was filtered and the solvent removed under reduced pressure giving 6.6 g of the product as a white foam. The structure was confirmed by NMR and mass spectroscopy.

INTERMEDIATES FOR EXAMPLES 16 AND 17

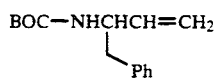

To a cold (−60°) suspension of 16.0 g (44.8 mmole) of methyltriphenylphosphonium bromide in 100 ml dry THF was added dropwise 28 ml (44.8 mmole) of a 1.6 M solution of n-butyl lithium in hexane over a period of 20 minutes. The reaction mixture was stirred for 15 minutes at −60°, followed by the dropwise addition of 10.4 g (40.73 mmole) of BOC-phenylalanal in 100 ml THF over a period of 30 minutes. The mixture was allowed to warm to room temperature, stirred for two hours, then poured into water. The aqueous mixture was extracted three times with Et₂O. The combined Et₂O layers were washed 0.5 N HCl, saturated NaHCO₃, and brine. Drying over MgSO₄ and removal of the solvent under reduced pressure gave the crude product. Chromatography on silica gel, eluting with a gradient of 10%–30% EtOAc in hexane gave 9.42 g of the product. The structure was confirmed by NMR and mass spectroscopy.

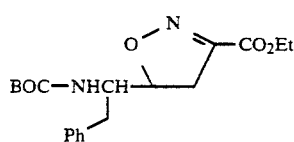
(Isomers A and B)

To a solution of 7.89 g (31.90 mmole) of

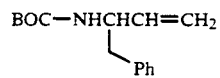

in 150 ml of Et₂O was added 10.15 g (67 mmole) of ethyl chlorooximinioacetate. To this reaction mixture was added 7.10 g (70.18 mmole) of Et₃N via a syringe pump over a period of 12 hours. The reaction mixture was then extracted with H₂O and saturated NaHCO₃. Drying over MgSO₄ and removal of the solvent under reduced pressure gave the crude product. Chromatography on silica gel, eluting with hexane/EtOAc (80/20) gave 5.18 g of the product (Isomer A) as a white solid. The structure was confirmed by NMR and mass spectroscopy.

Continued elution from the column gave 3.16 g of Isomer B as a white solid. The structure was confirmed by NMR and mass spectroscopy.

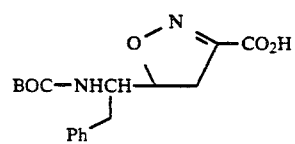

To a solution of 4.14 g (11.42 mmole) of

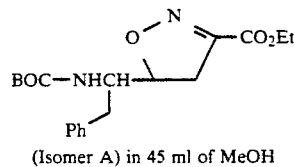
(Isomer A) in 45 ml of MeOH was added 7 ml of 2 N NaOH and the mixture stirred at room temperature for one hour. The reaction mixture was poured into water, cooled to 5°, and acidified to pH 2 with 0.5 N HCl. The aqueous layer was extracted four times with CH₂Cl₂ and the combined organic layers dried over MgSO₄. Removal of the solvent under reduced pressure gave 3.09 g of the product. The structure was confirmed by NMR and mass spectroscopy.

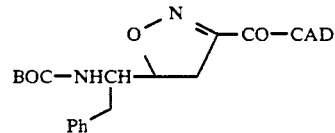

A solution of 2.5 g (7.48 mmole) of

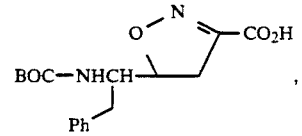

0.83 g (8.22 mmole) of Et₃N, 2.18 g (8.97 mmole) of CAD, and 1.21 g (8.97 mmole) of HOBT in 40 ml CH₂Cl₂ was cooled in ice and treated with 1.69 g (8.22 mmole) of DCC. After stirring at 0° for one hour, the mixture was left at room temperature for two days. The solvent was removed under reduced pressure and the residue taken up in EtOAc and filtered. Removal of the solvent gave the crude product. Chromatography on silica gel, eluting with a gradient of 1% to 1.5% MeOH in CH₂Cl₂ gave 4.29 g of the product. The structure was confirmed by NMR and mass spectroscopy.

What is claimed is:

1. A compound of formula

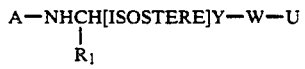

or a pharmaceutically acceptable acid addition salt thereof wherein:

A is SMO;
R₁ is CH₂Ph,

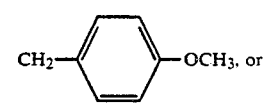

-continued

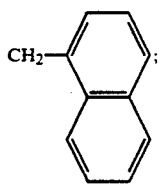

[isostere] is [CHOHCH$_2$], [COCH$_2$], [CHOH-CHOH], [CH=CH],

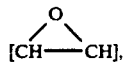

[CH$_2$NH], [CH$_2$NOH], [CH$_2$S], [CH$_2$(NH$_2$)CH$_2$], [CH$_2$SO$_2$], [CH$_2$CH$_2$],

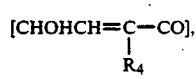

[CHOHCHOHCHOHCO] or [CH$_2$O] wherein R$_4$ is H, loweralkyl, lower alkenyl, lower alkynyl, CO$_2$R$_3$, or arylmethyl.

Y is absent,

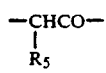

wherein
R$_5$ is hydrogen, OR$_6$, S(O)$_n$R$_6$, NR$_7$R$_8$ or NHCOR$_9$ wherein R$_6$ is lower alkyl, lower alkenyl, lower alkynyl, or aryl, n is an integer of from 0 to 2, R$_7$ and R$_8$ are each independently hydrogen, lower alkyl, lower alkenyl, lower alkyl, or aryl, R$_9$ is hydrogen, lower alkyl or aryl with the proviso that when [ISOSTERE] is

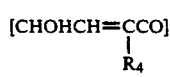

or [CHOHCHOHCHOHCO], Y is absent;
W is CAD, CAH, DECYS, DEKCYS, DFSTA, DFKSTA, ASTA, ACYS or

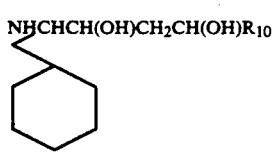

wherein
R$_{10}$ is lower alkyl or alkenyl; and
U is absent, MBA, NHCH$_2$Ph, NHC$_4$H$_9$, NHCH$_3$ or

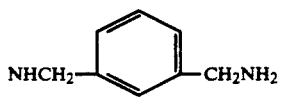

with the proviso that when W is CAD, CAH or

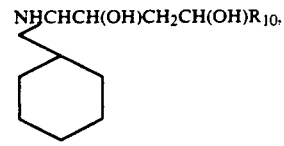

U is absent.

2. A compound of formula $$A-NHCH[ISOSTERE]Y-W-U \quad | \quad R_1 \qquad I$$

or a pharmaceutically acceptable acid salt thereof wherein:
A is SMO;
R$_1$ is CH$_2$Ph,

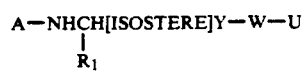

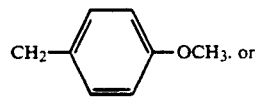

[isostere] is [CHOHCH$_2$], [COCH$_2$], [CHOH-CHOH], [CH(NH$_2$)CH$_2$], [CH=CH],

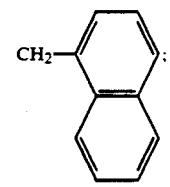

[CH$_2$NH], [CH$_2$NOH], [CH$_2$S], [CH$_2$SO$_2$], [CH$_2$CH$_2$], or [CH$_2$O];

Y is

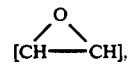

wherein R$_5$ is H, loweralkyl, lower alkenyl, lower alkynyl, or arylmethyl.

W is CAD, CAH, DECYS, DEKCYS, DFSTA, DFKSTA, ASTA, ACYS or NHCHCH(OH)CH$_2$CH(OH)R$_{10}$ wherein
R$_{10}$ is lower alkyl or alkenyl; and
U is absent, MBA, NHCH$_2$Ph, NHC$_4$H$_9$, NHCH$_3$ or

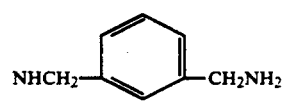

with the proviso that when W is CAD, CAH or NHCHCH(OH)CH$_2$CH(OH)R$_{10}$, U is absent.

3. A compound of formula

A—NHCH[ISOSTERE]Y—W—U  I
  |
  R₁ or a pharmaceutically acceptable acid salt thereof wherein:
A is SMO;
R₁ is CH₂Ph,

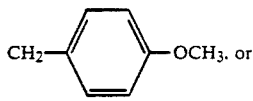

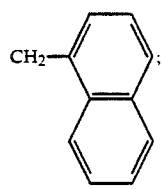

[isostere] is [CHOHCH₂], [COCH₂], [CH=NH], [CHOHCH₂CHCO], [CHOHCH=C(CH₃)CO], [CHOHCH=C(C₄H₉)CO], or [CHOHCH=C(CH₂Ph)CO],
with the proviso that Y is absent when [ISOSTERE] is [CHOHCH=CHCO], [CHOHCH=C(C₄H₉)CO], [CHOHCH=C(CH₃)CO], or [CHOHCH=C(CH₂Ph)CO],
Y is

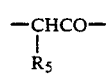

wherein R₅ is hydrogen, OCH₃, OC₃H₇, OCH₂CH=CH₂, OCH₂C=CH, SCH₃, SC₃H₇, SCH₂CH=CH₂, SCH₂C=CH, NH₂, NHCH₃, N(CH₃)₂, or NHCOCH₃;
W is CAD, CAH, DFKCYS, DFKSTA,

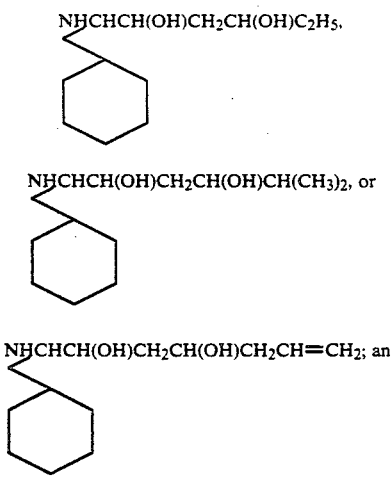

U is absent, NHC₄H₉, or NHCH₂—⌬—CH₂NH₂ with the proviso that U is absent when W is CAD, CAH, or

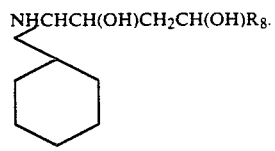

4. A compound according to claim 2 wherein Y is

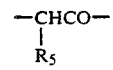

5. A compound selected from the group consisting of:
SMO-PHEΨ[CHOHCH=CHCO]CAD,
SMO-PHEΨ[CH=CH]GLY-CAD,

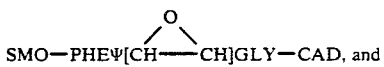

SMO-PHEΨ[CH₂NH]GLY-CAD.

6. A compound SMO-PHEΨ[CH(OTBDMS)CH₂G-LY-CAD.

7. A pharmaceutical composition comprising a renin-inhibitory effective amount of a compound as claimed in claim 1 together with a pharmaceutically acceptable carrier.

8. A pharmaceutical composition comprising a renin-associated hyperaldosteronism-inhibitory effective amount of a compound as claimed in claim 1 together with a pharmaceutically acceptable carrier.

9. A pharmaceutical composition comprising an amount effective for treating renin-associated congestive heart failure of a compound as claimed in claim 1 together with a pharmaceutically acceptable carrier.

10. A pharmaceutical composition comprising a amount effective for treating glaucoma of a compound as claimed in claim 1 together with a pharmaceutically acceptable carrier.

11. A pharmaceutical composition comprising a renin-inhibitory effective amount of a compound as claimed in claim 2 together with a pharmaceutically acceptable carrier.

12. A pharmaceutical composition comprising a renin-associated hyperaldosteronism-inhibitory effective amount of a compound as claimed in claim 2 together with a pharmaceutically acceptable carrier.

13. A pharmaceutical composition comprising an amount effective for treating renin-associated congestive heart failure of a compound as claimed in claim 2 together with a pharmaceutically acceptable carrier.

14. A pharmaceutical composition comprising an amount effective for treating glaucoma of a compound as claimed in claim 2 together with a pharmaceutically acceptable carrier.

15. A method of treating renin-associated hypertension which comprises administering to a mammal a pharmaceutical composition as claimed in claim 1.

16. A method of treating renin-associated hyperaldosteronism which comprises administering to a mammal a pharmaceutical composition as claimed in claim 8.

17. A method of treating renin-associated congestive heart failure which comprises administering to a mammal a pharmaceutical composition as claimed in claim 9.

18. A method of determining the presence of renin-associated hypertension in a patient, comprising administering to such a patient, at a hypertensive dosage level and as a single dose, a compound according to claim 1, followed by monitoring of said patient's blood pressure.

19. A method for treating glaucoma which comprises administering to a mammal a pharmaceutical composition as claimed in claim 10.

20. A method of treating renin-associated hypertension which comprises administering to a mammal a pharmaceutical composition as claimed in claim 2.

21. A method of treating renin-associated hyperaldosteronism which comprises administering to a mammal a pharmaceutical composition as claimed in claim 12.

22. A method of treating renin-associated congestive heart failure which comprises administering to a mammal a pharmaceutical composition as claimed in claim 13.

23. A method of determining the presence of renin-associated hypertension in a patient, comprising administering to such a patient, at a hypertensive dosage level and as a single dose, a compound according to claim 2, followed by monitoring of said patient's blood pressure.

24. A method for treating glaucoma which comprises administering to a mammal a pharmaceutical composition as claimed in claim 14.

25. A compound selected from the group consisting of:

SMO-PHEΨ[COCH$_2$]GLY-CAD and
SMO-PHEΨ[CHOHCH$_2$]GLY-CAD.

* * * * *